US012702314B2

(12) United States Patent
Harada et al.

(10) Patent No.: US 12,702,314 B2
(45) Date of Patent: Aug. 11, 2026

(54) CUFF STRUCTURE AND BLOOD PRESSURE MEASUREMENT DEVICE

(71) Applicant: OMRON HEALTHCARE Co., Ltd., Kyoto (JP)

(72) Inventors: Masaki Harada, Kyoto (JP); Yoshihide Tokko, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 989 days.

(21) Appl. No.: 17/930,958

(22) Filed: Sep. 9, 2022

(65) Prior Publication Data

US 2023/0000373 A1 Jan. 5, 2023

Related U.S. Application Data

(63) Continuation of application No. PCT/JP2021/005331, filed on Feb. 12, 2021.

(30) Foreign Application Priority Data

Mar. 16, 2020 (JP) ................................ 2020-045264

(51) Int. Cl.
*A61B 5/022* (2006.01)
*A61B 5/00* (2006.01)

(52) U.S. Cl.
CPC .......... *A61B 5/02233* (2013.01); *A61B 5/681* (2013.01)

(58) Field of Classification Search
CPC ........................... A61B 5/02233; A61B 5/681
See application file for complete search history.

(56) References Cited

U.S. PATENT DOCUMENTS 5,101,829 A 4/1992 Fujikawa et al.
5,131,400 A 7/1992 Harada et al.
6,336,901 B1 * 1/2002 Itonaga .................. A61B 5/681 600/499

(Continued)

FOREIGN PATENT DOCUMENTS

CN 110267588 A 9/2019
CN 115066202 A 9/2022
JP 2003-24286 A 1/2003

(Continued)

OTHER PUBLICATIONS

English-language machine translation of JP-3922087-B2 (Year: 2025).*
Office Action issued on Mar. 19, 2024 in corresponding JP patent application No. 2020-049160.
Indian Office Action Issued for corresponding Indian Application No. 202217049975, Dated Apr. 3, 2023.

(Continued)

*Primary Examiner* — Andrey Shostak
(74) *Attorney, Agent, or Firm* — Colson Law Group, PLLC

(57) ABSTRACT

To provide a cuff structure capable of improving measurement accuracy of blood pressure, and a blood pressure measurement device. A cuff structure includes a sensing cuff configured in shape that is long in one direction and coming into contact with a region of a wrist where an artery is present, a pressing cuff configured in a shape that is long in one direction, provided on a side of the sensing cuff opposite from the wrist side surface, and pressing the sensing cuff against the wrist by being inflated, and a wall portion provided along at least one edge portion along a longitudinal direction of the sensing cuff and having a leading end surface on the wrist side coming into contact with the wrist.

2 Claims, 10 Drawing Sheets

(56) References Cited

U.S. PATENT DOCUMENTS

2005/0177047 A1* 8/2005 Harpas .................. A61B 5/489
600/490
2019/0365259 A1* 12/2019 Nishikawa ......... A61B 5/02233

FOREIGN PATENT DOCUMENTS

| | | | | |
|---|---|---|---|---|
| JP | 3922087 | B2 * | 5/2007 | |
| JP | 2009-213767 | A | 9/2009 | |
| JP | 2018-161382 | A | 10/2018 | |
| JP | 2019-118418 | A | 7/2019 | |
| WO | 0049943 | A1 | 8/2000 | |
| WO | WO-2018179645 | A1 * | 10/2018 | ............. A61B 5/681 |

OTHER PUBLICATIONS

Office Action issued on Mar. 12, 2024 in corresponding JP patent application No. 2020-045264.

International Search Report for International Application No. PCT/JP2021/005331, dated Apr. 13, 2021.

International Preliminary Report on Patentability for International Application No. PCT/JP2021/005331, dated Jan. 7, 2022.

Office Action issued on Dec. 23, 2024 in corresponding JP patent application No. 202180018136.3.

Office Action issued on Dec. 23, 2024 in corresponding CN patent application No. 202180018136.3.

International Preliminary Report on Patentability Issued for International Application No. PCT/JP2021/005331, Dated Jan. 7, 2022.

* cited by examiner

[FIG. 7]
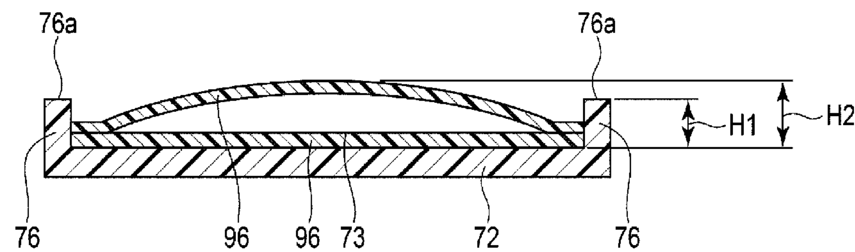
[FIG. 8]
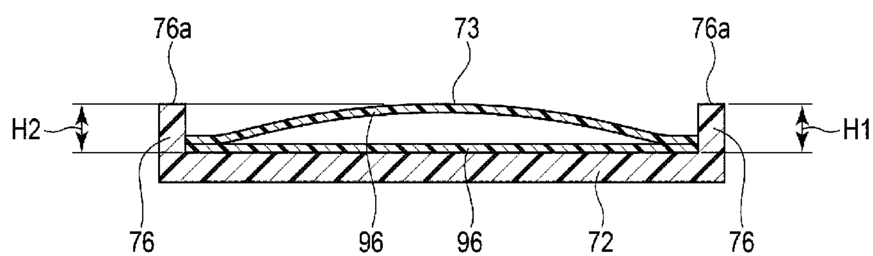
[FIG. 9]
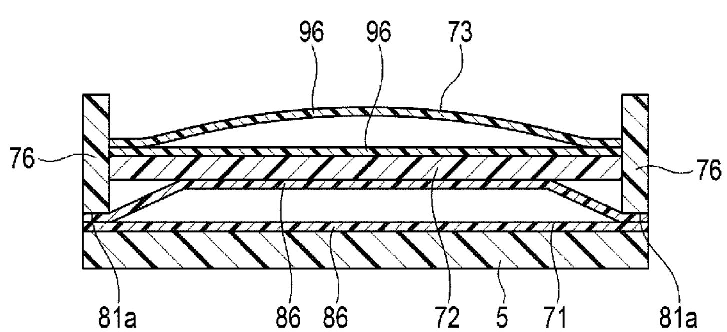
[FIG. 10]
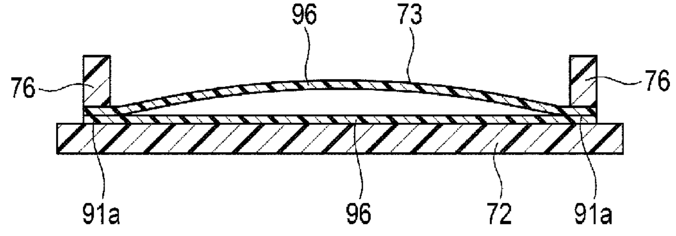

[FIG. 11]
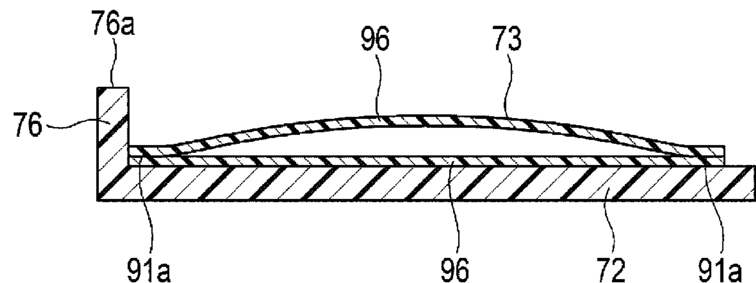
[FIG. 12]
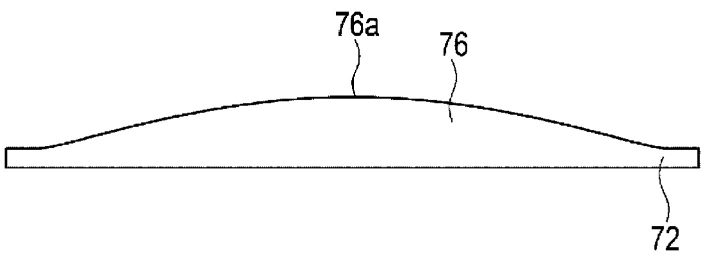
[FIG. 13]
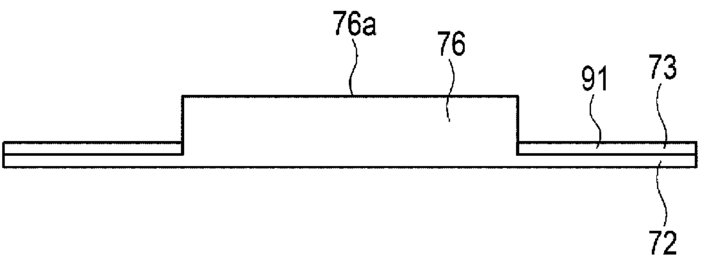
[FIG. 14]
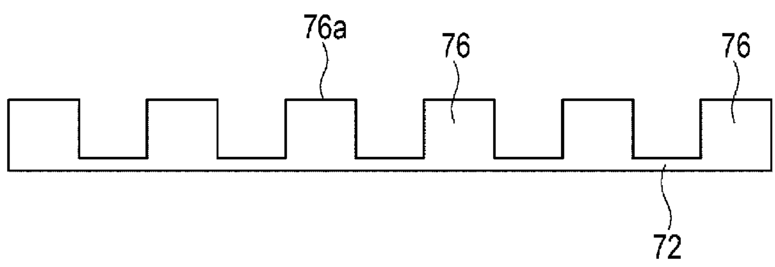

[FIG. 15]
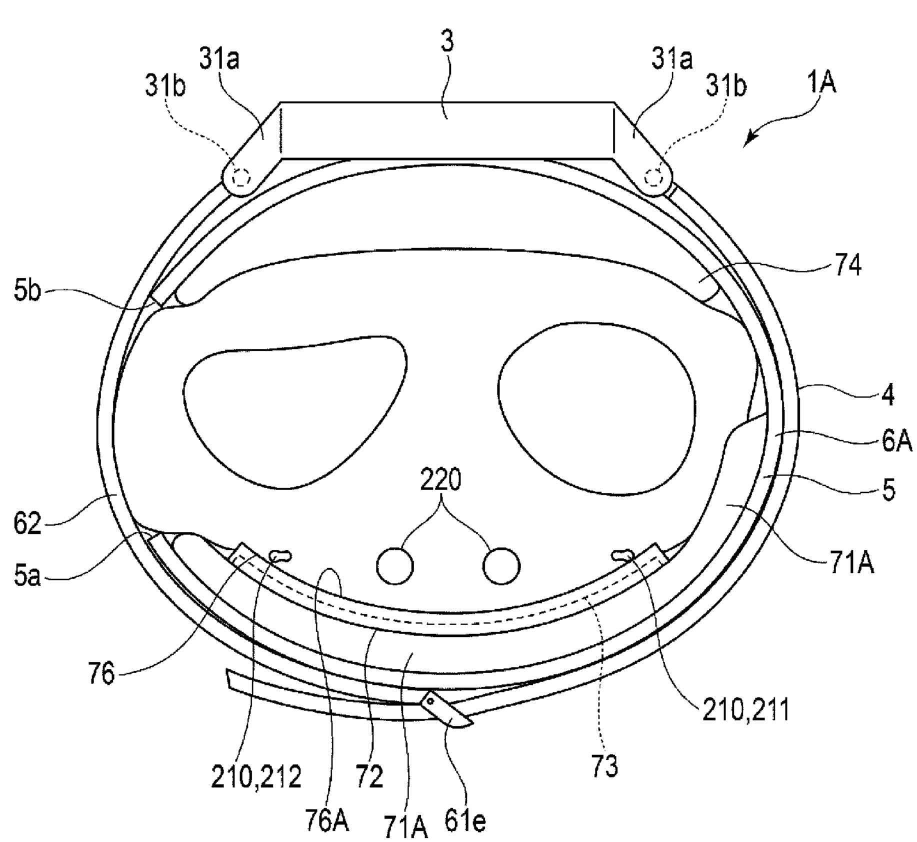

[FIG. 16]
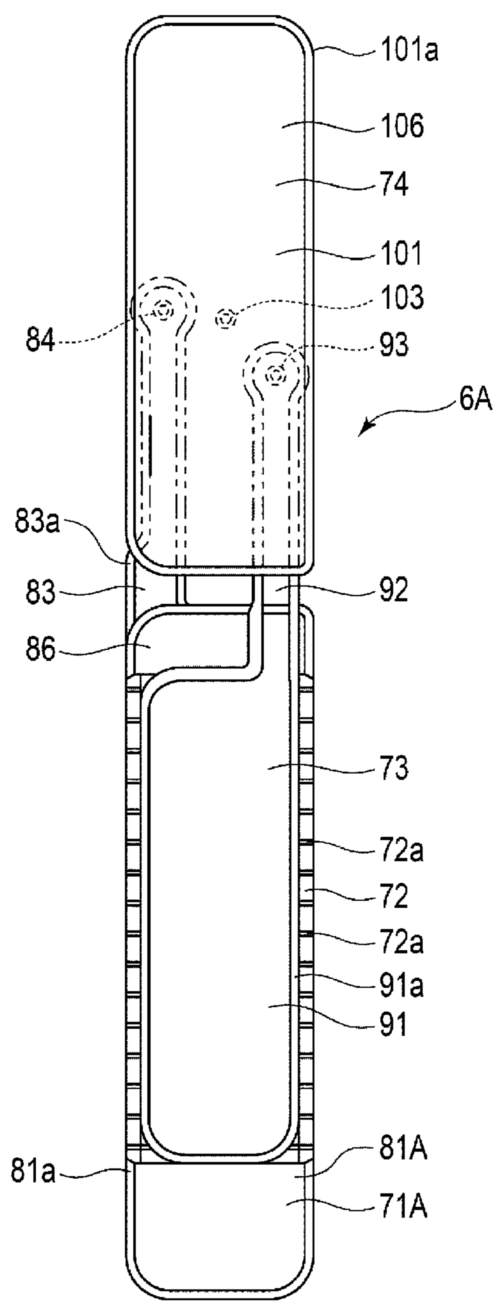

CUFF STRUCTURE AND BLOOD PRESSURE MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2021/005331, filed Feb. 12, 2021, which application claims priority to Japanese Patent Application No. 2020-045264, filed Mar. 16, 2020, which applications are incorporated herein by reference in their entireties.

TECHNICAL FIELD

The present invention relates to a cuff structure used in a blood pressure measurement device used for blood pressure measurement, and a blood pressure measurement device.

BACKGROUND ART

In recent years, a blood pressure measurement device for measuring blood pressure has been used to monitor health status at home, as well as in medical facilities. A blood pressure measurement device detects vibration of the artery wall to measure blood pressure by, for example, inflating and contracting a cuff wrapped around an upper arm, a wrist, or the like of a living body and detecting the pressure of the cuff using a pressure sensor.

As such a blood pressure measurement device, a so-called integral type is known in which a cuff is integrated with a device main body feeding a fluid to the cuff. Further, as the integral type blood pressure measurement device, a wearable device to be mounted on a wrist is also considered (for example, see Patent Document 1: Japanese Patent Application No.: JP 2019-118418 A).

Technical Problem

There are tendons, bones and muscles in a wrist. Due to the shape of a living body such as the tendons, bones, and muscles, unevenness occurs in a region where an artery of the wrist is present. Since the shape of the tendons, bones, and muscles vary depending on the user, the uneven shape of the region of the wrist with which a sensing cuff is brought into contact varies depending on the user.

In a state where blood pressure is measured, air in a sensing cuff is required to be evenly present in the sensing cuff.

The above-described blood pressure measurement device is required to improve the measurement accuracy of blood pressure.

Thus, an object of the present invention is to provide a cuff structure capable of improving the accuracy of blood pressure detection, and the blood pressure measurement device.

Solution to Problem

According to an aspect, a cuff structure is provided that includes a sensing cuff configured in a shape that is long in one direction, the sensing cuff configured to come into contact with a region of a wrist where an artery is present, a pressing cuff configured in a shape that is long in one direction and, the pressing cuff provided on a side of the sensing cuff opposite from the wrist side surface, the pressing cuff configured to press the sensing cuff against the wrist by being inflated, and a wall portion provided along at least one edge portion along a longitudinal direction of the sensing cuff, the wall portion having a leading end surface configured to come into contact with the wrist.

The sensing cuff and the pressing cuff are inflated by being fed with the fluid, and include a bag-like structure such as an air bag.

According to this aspect, the blood pressure measurement device is mounted on the wrist and the pressing cuff is inflated so that a wall portion presses the wrist. Since the wall portion presses the wrist, the unevenness of the region of the wrist where the artery is present can be reduced. Here, the unevenness of the wrist means unevenness caused by a portion of a living body such as a tendon, a muscle, and a bone of the wrist. By reducing the unevenness of the wrist, the sensing cuff to which air is supplied can be adhered to the region of the wrist where the artery is present by the pressure of the sensing cuff to the wrist caused by the inflation of the pressing cuff.

Further, since the unevenness of the wrist is reduced, even when the sensing cuff to which air is supplied is pressed against the wrist by the inflated pressing cuff, it is possible to prevent the sensing cuff from being collapsed. Here, the collapse means that the wrist side and the pressing cuff side of the inner surface of the sensing cuff come into contact with each other. By preventing the collapse of the sensing cuff, the fluid can be uniformly present in the sensing cuff.

Further, since the wall portion presses the wrist, the wrist follows the end surface of the wall portion. As a result, the sensing cuff can be suitably adhered to the wrist.

In this manner, the sensing cuff can be suitably adhered to the region of the wrist where the artery is present, and the fluid can be uniformly present in the sensing cuff, and thus the accuracy of the blood pressure measurement can be improved.

In addition, since the wall portion is configured to face the tendon that is present between the radial artery and the ulnar artery of the wrist in a state where the blood pressure measurement device is mounted on the wrist, the tendon can be pushed by the wall portion. By pushing the tendon by the wall portion, the sensing cuff can be adhered to the wrist in a wide range including the radial artery and the ulnar artery.

Further, when a pair of wall portions is provided along each of edge portions along the longitudinal direction of the sensing cuff, the pair of wall portions presses the wrist. Since the wrist is pressed by the pair of wall portions, a portion of the wrist between the pair of wall portions follows an end surface of the wall portions. Thus, the region of the wrist that follows the end surface of the wall portions can be increased, so that the sensing cuff can be more suitably adhered to the wrist.

In the cuff structure of the aspect described above, a cuff structure is provided that includes a back plate provided between the pressing cuff and the sensing cuff, wherein the wall portion is provided on the back plate.

According to this aspect, the wall portion is supported by the back plate, and thus the wall portion can be stably pressed against the wrist.

Furthermore, a number of parts of the cuff structure can be prevented from increasing. Therefore, the efficiency of the assembling work of the blood pressure measurement device can be improved.

In the cuff structure of the aspect described above, a cuff structure is provided wherein a plurality of grooves orthogonal to the longitudinal direction are formed on the leading end surface.

According to this aspect, the wall portion is easily deformed along the circumferential direction of the wrist. As a result, it is possible to prevent the work of mounting the blood pressure measurement device on the wrist from being difficult.

In the cuff structure of the aspect described above, a cuff structure is provided wherein the wall portion has a height such that the wall portion protrudes beyond the sensing cuff and the sensing cuff is adhered to the wrist in a state where the sensing cuff is inflated.

According to this aspect, when the pressing cuff is inflated by supplying air to the sensing cuff after the blood pressure measurement device is mounted on the wrist, the sensing cuff comes into contact with the wrist after the wall portion pushes the region of the wrist where the artery is present. As a result, it is possible to suitably adhere the sensing cuff to the region of the wrist where the artery is present.

According to an aspect, a blood pressure measurement device is provided that includes a device main body, a curler provided on the device main body, and a cuff structure provided on the curler, the cuff structure including a sensing cuff configured in a shape that is long in one direction, the sensing cuff configured to come into contact with a region of a wrist where an artery is present, a pressing cuff configured in a shape that is long in one direction, the pressing cuff provided on a side of the sensing cuff opposite from the wrist side surface, the pressing cuff configured to press the sensing cuff against the wrist by being inflated, and a wall portion provided along at least one edge portion along a longitudinal direction of the sensing cuff, the wall portion having a leading end surface configured to come into contact with the wrist.

According to this aspect, the blood pressure measurement device is mounted on the wrist and the pressing cuff is inflated so that a wall portion presses the wrist. Since the wall portion presses the wrist, the unevenness of the region of the wrist where the artery is present can be reduced. Here, the unevenness of the wrist means unevenness caused by a portion of a living body such as a tendon, a muscle, and a bone of the wrist. By reducing the unevenness of the wrist, the sensing cuff to which air is supplied can be adhered to the region of the wrist where the artery is present by the pressure of the sensing cuff to the wrist caused by the inflation of the pressing cuff.

Further, since the unevenness of the wrist is reduced, even when the sensing cuff to which air is supplied is pressed against the wrist by the inflated pressing cuff, it is possible to prevent the sensing cuff from being collapsed. Here, the collapse means that the wrist side and the pressing cuff side of the inner surface of the sensing cuff come into contact with each other. By preventing the collapse of the sensing cuff, the fluid can be uniformly present in the sensing cuff.

Further, since the wall portion presses the wrist, the wrist follows the end surface of the wall portion. As a result, the sensing cuff can be suitably adhered to the wrist.

In this manner, the sensing cuff can be suitably adhered to the region of the wrist where the artery is present, and the fluid can be uniformly present in the sensing cuff, and thus the accuracy of the blood pressure measurement can be improved.

In addition, since the wall portion is configured to face the tendon that is present between the radial artery and the ulnar artery of the wrist in a state where the blood pressure measurement device is mounted on the wrist, the tendon can be pushed by the wall portion. By pushing the tendon by the wall portion, the sensing cuff can be adhered to the wrist in a wide range including the radial artery and the ulnar artery.

Further, when a pair of wall portions is provided along each of edge portions along the longitudinal direction of the sensing cuff, the pair of wall portions presses the wrist. Since the wrist is pressed by the pair of wall portions, a portion of the wrist between the pair of wall portions follows an end surface of the wall portions. Thus, the region of the wrist that follows the end surface of the wall portions can be increased, so that the sensing cuff can be more suitably adhered to the wrist.

Advantageous Effects of Invention

The present invention can provide a cuff structure capable of improving measurement accuracy of blood pressure, and a blood pressure measurement device.

BRIEF DESCRIPTION OF DRAWINGS

Various embodiments are disclosed, by way of example only, with reference to the accompanying schematic drawings in which corresponding reference symbols indicate corresponding parts, in which:

FIG. 7 is a cross-sectional view illustrating a configuration of a cuff structure according to a modified example of the present invention;

FIG. 8 is a cross-sectional view illustrating the configuration of the cuff structure according to the modified example of the present invention;

FIG. 9 is a cross-sectional view illustrating the configuration of the cuff structure according to the modified example of the present invention;

FIG. 10 is a cross-sectional view illustrating the configuration of the cuff structure according to the modified example of the present invention;

FIG. 11 is a cross-sectional view illustrating the configuration of the cuff structure according to the modified example of the present invention;

FIG. 12 is a side view illustrating a configuration of a back plate and a wall portion according to the modified example of the present invention;

FIG. 13 is a side view illustrating the configuration of the back plate and the wall portion according to the modified example of the present invention;

FIG. 14 is a side view illustrating the configuration of the back plate and the wall portion according to the modified example of the present invention;

FIG. 15 is an explanatory view illustrating a state where the blood pressure measurement device according to the modified example of the present invention is mounted on the wrist; and, FIG. 16 is a plan view illustrating a configuration of the cuff structure of the blood pressure measurement device.

DESCRIPTION OF EMBODIMENTS

An example of a blood pressure measurement device 1 according to an embodiment of the present invention is described below with reference to FIG. 1 to FIG. 6.

Figure 1:
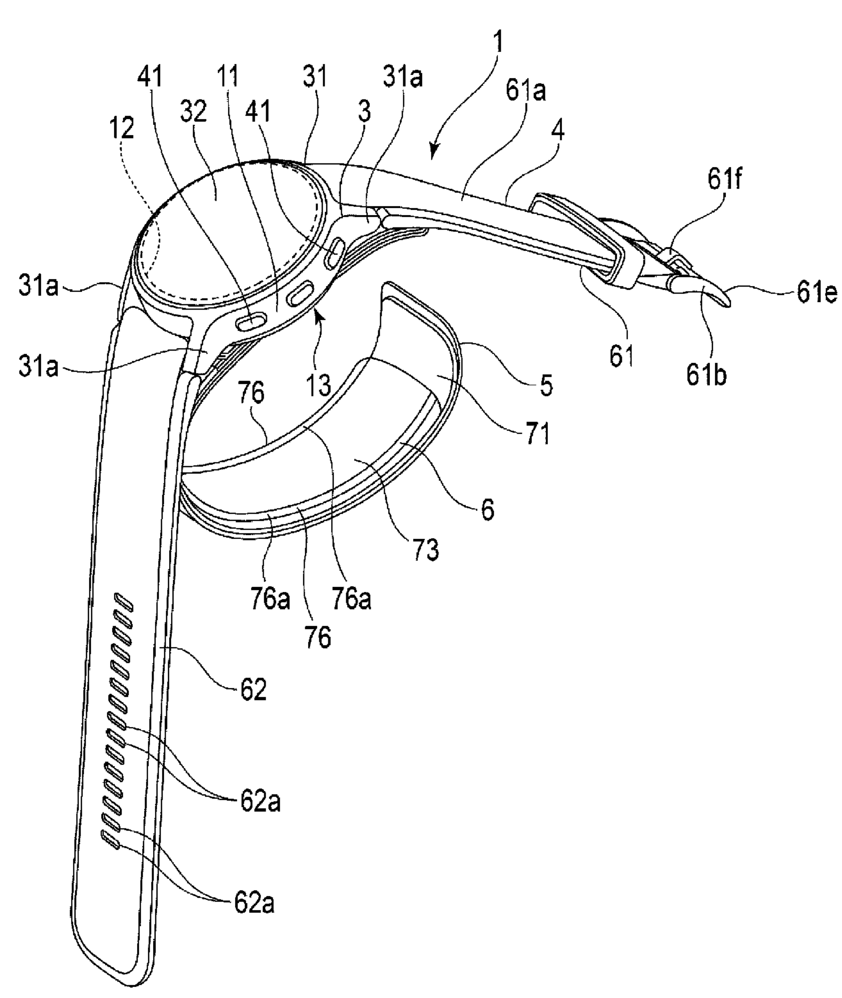
FIG. 1 is a perspective view illustrating a configuration of a blood pressure measurement device according to an embodiment of the present invention.
Figure 2:
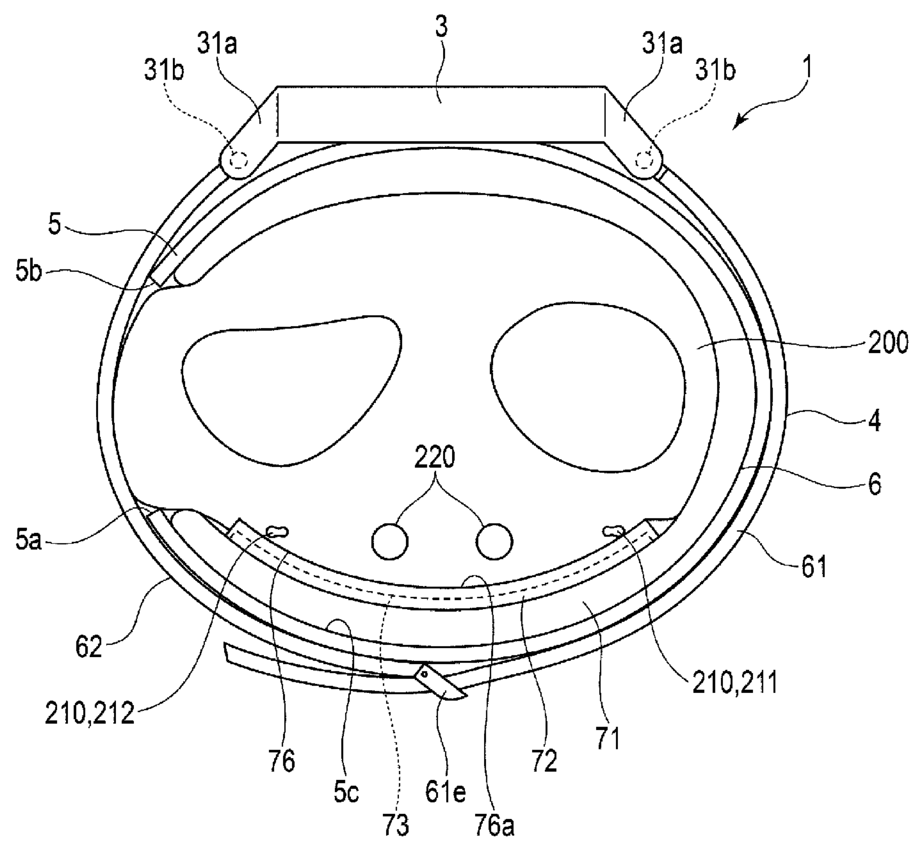
FIG. 2 is an explanatory view illustrating a state where the blood pressure measurement device is mounted on a wrist.
Figure 3:
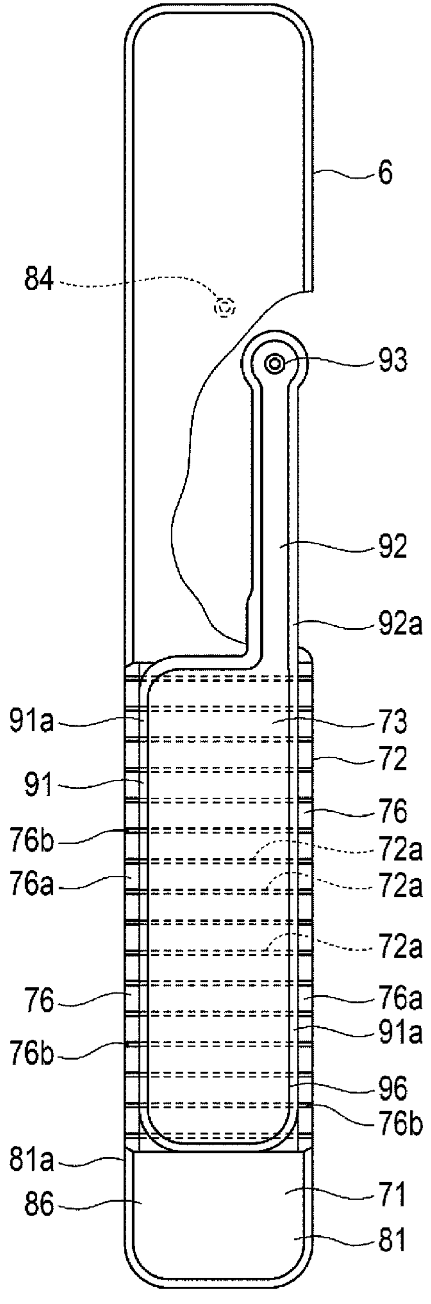
FIG. 3 is a plan view illustrating a configuration of a cuff structure of the blood pressure measurement device.

FIG. 1 is a perspective view illustrating the configuration of the blood pressure measurement device 1. FIG. 2 is an explanatory view illustrating a state where the blood pressure measurement device 1 is mounted on a wrist 200. Here, mounting the blood pressure measurement device 1 on the wrist 200 means fixing the blood pressure measurement device 1 to the wrist 200 by attaching the blood pressure measurement device 1 to the wrist 200 and tightening a belt 4 that is an example of a fixing tool. FIG. 3 is a plan view illustrating a configuration of a cuff structure 6 of the blood pressure measurement device 1. In FIG. 3, a pressing cuff 71 of the cuff structure 6 illustrates a state where a portion of the pressing cuff 71 is cut off.

Figure 4:
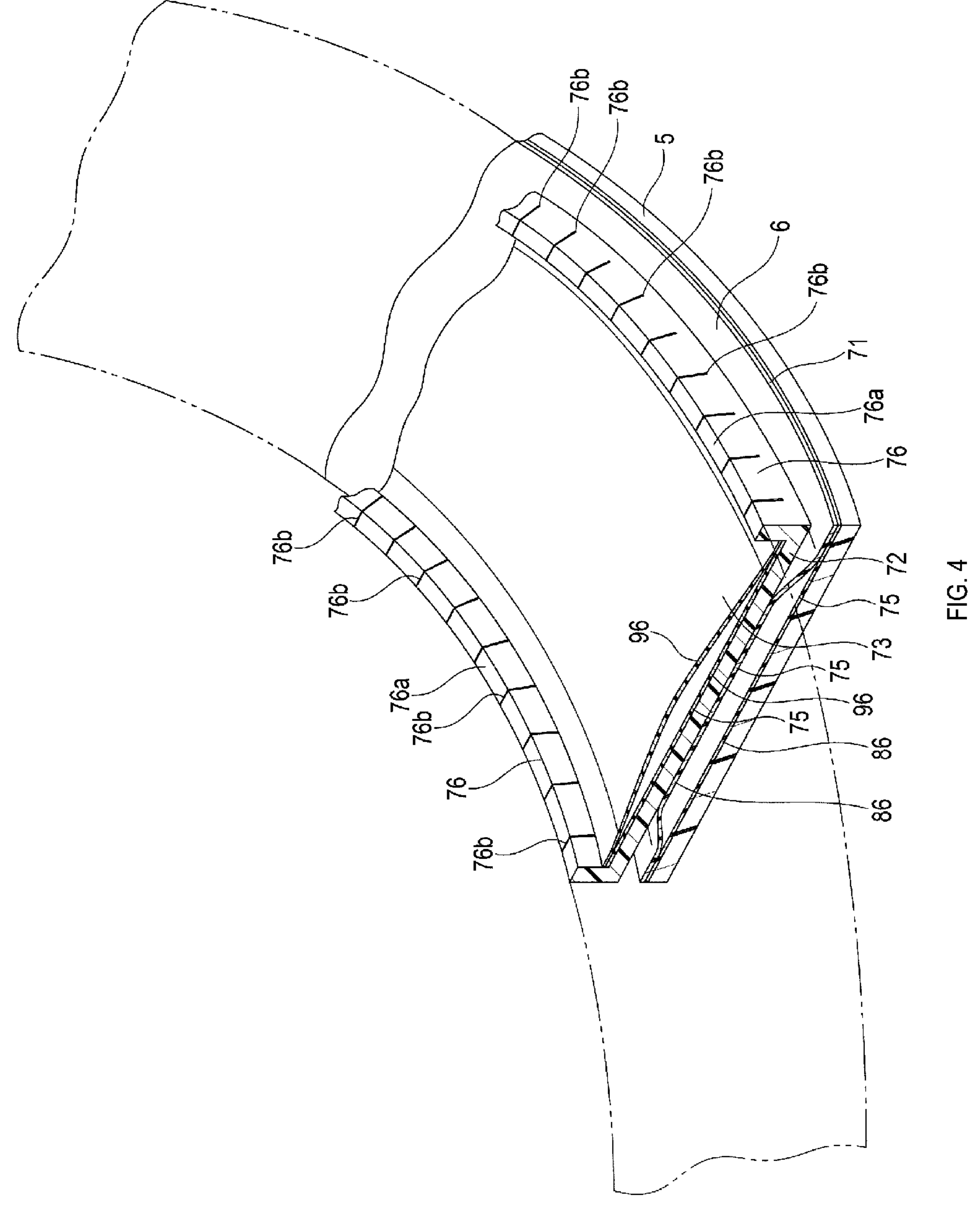
FIG. 4 is a perspective view illustrating a portion of a curler and the cuff structure of the blood pressure measurement device.
Figure 5:
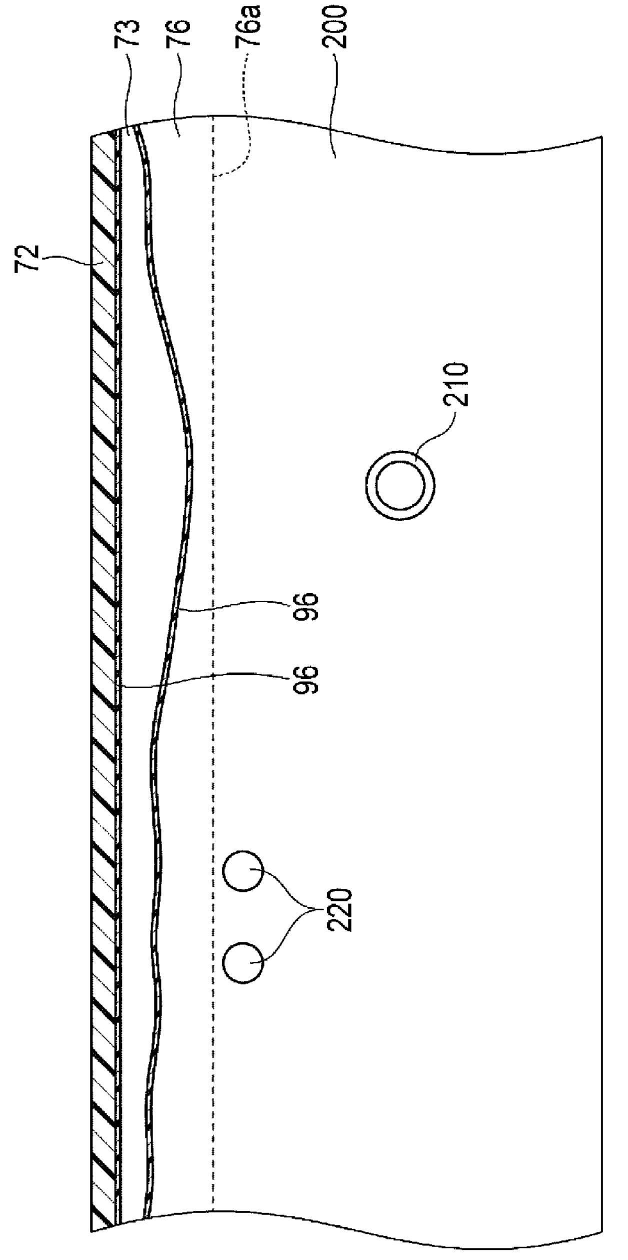
FIG. 5 is a cross-sectional view schematically illustrating a state where the blood pressure measurement device is mounted on the wrist.
Figure 6:
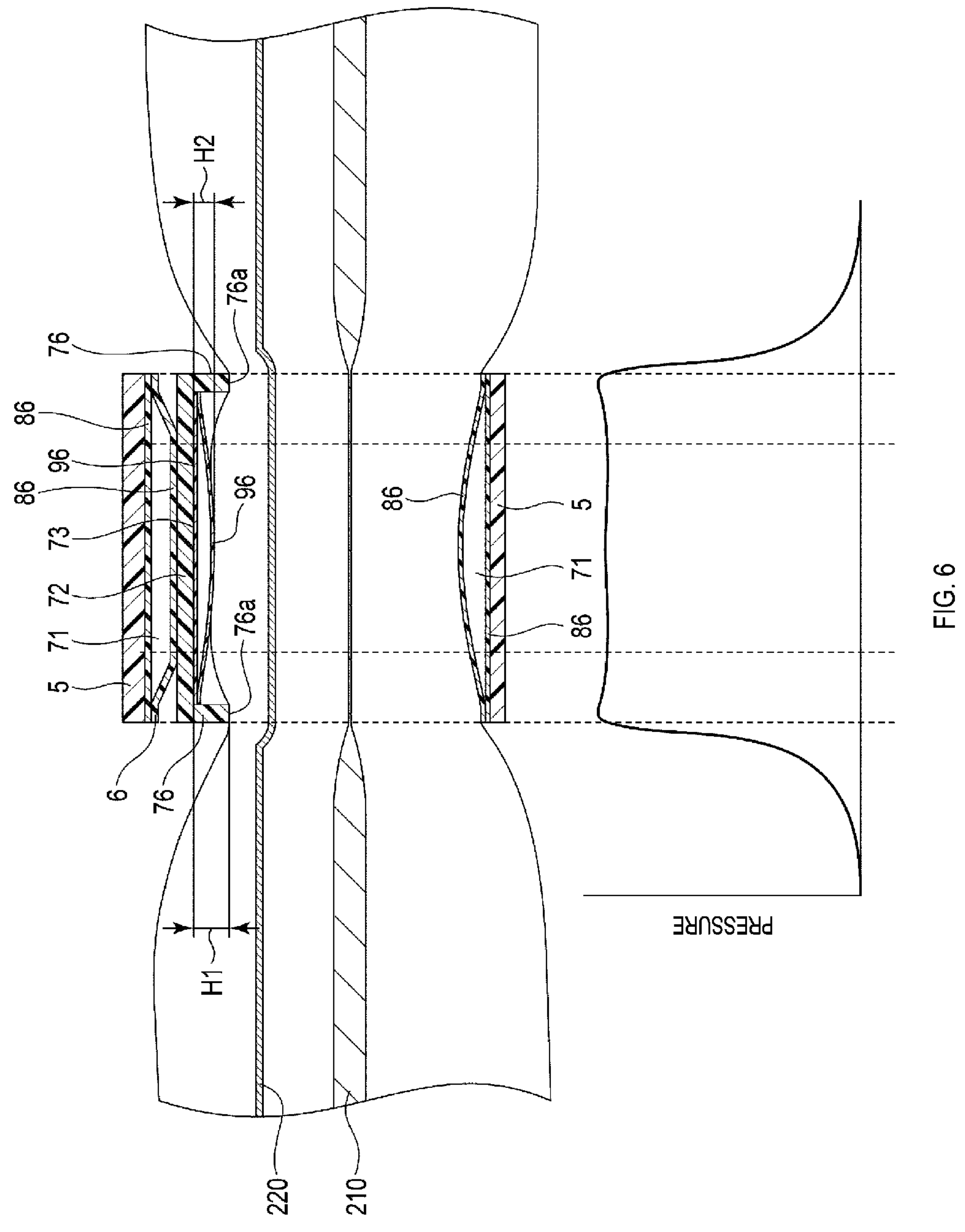
FIG. 6 is an explanatory view illustrating a state where the blood pressure measurement device is mounted on the wrist and pressure acting on the wrist.

FIG. 4 is a perspective view illustrating a portion of a curler 5 and the cuff structure 6 of the blood pressure measurement device 1. FIG. 5 is an explanatory view illustrating a state where the blood pressure measurement device 1 is mounted on the wrist 200. FIG. 6 is an explanatory view schematically illustrating a state where the blood pressure measurement device 1 is mounted on the wrist 200 and pressure acting on the wrist 200.

As illustrated in FIG. 1 and FIG. 2, the blood pressure measurement device 1 includes a device main body 3, the belt 4 for fixing the device main body 3 to the wrist 200, the curler 5 disposed between the belt 4 and the wrist 200, and the cuff structure 6.

The device main body 3 includes, for example, a case 11, a display unit 12, and an operation unit 13. In addition, the device main body 3 includes, in the case 11, a pump for inflating the cuff structure 6, a flow path portion for fluidly connecting the pump and the cuff structure 6, and a control board.

The case 11 includes an outer case 31 and a windshield 32 that covers an opening of the outer case 31 on a side opposite to the wrist 200 side.

The outer case 31 is formed in a cylindrical shape. The outer case 31 includes pairs of lugs 31*a* provided at respective symmetrical positions in the circumferential direction of an outer circumferential surface, and spring rods 31*b* each provided between each of the two pairs of lugs 31*a*.

The windshield 32 is, for example, a circular glass plate.

The display unit 12 is disposed directly below the windshield 32. The display unit 12 is electrically connected to the control board. The display unit 12 is, for example, a liquid crystal display or an organic electroluminescence display. The display unit 12 displays various types of information including the date and time and measurement results of blood pressure values such as the systolic blood pressure and diastolic blood pressure, heart rate, and the like.

The operation unit 13 is configured to be capable of receiving an instruction input from a user. For example, the operation unit 13 includes a plurality of buttons 41 provided at the case 11 and a sensor that detects the operation of the buttons 41. As the plurality of buttons 41, for example, three buttons are provided.

The belt 4 is an example of a fixing tool that fixes the blood pressure measurement device 1 in a state where the blood pressure measurement device 1 is mounted on the wrist 200. The belt 4 includes a first belt 61 provided on one pair of lugs 31*a* and the spring rod 31*b*, and a second belt 62 provided on the other pair of lugs 31*a* and the spring rod 31*b*. The belt 4 is wrapped around the wrist 200 with the curler 5 in between.

The first belt 61 is referred to as a so-called a parent and is configured like a band capable of being joined to the second belt 62. The first belt 61 includes a belt portion 61*a* and a buckle 61*b*. The belt portion 61*a* is configured like a band. The belt portion 61*a* is formed of an elastically deformable resin material.

One end of the belt portion 61*a* is supported by one spring rod 31*b*. The buckle 61*b* is provided at the other end of the belt portion 61*a*. The buckle 61*b* includes a frame body 61*e* in a rectangular frame shape and a prong 61*f* rotatably attached to the frame body 61*e*.

The second belt 62 is referred to as a so-called blade tip, and is configured in a band-like shape having a width at which the second belt 62 can be inserted into the frame body 61*e*. The second belt 62 is formed of an elastically deformable resin material. In addition, the second belt 62 includes a plurality of small holes 62*a* into which the prong 61*f* is inserted. One end of the second belt 62 is supported by the other spring rod 31*b*.

The second belt 62 is inserted into the frame body 61*e*, and the prong 61*f* is inserted into the small hole 62*a*, and thus the first belt 61 and the second belt 62 are integrally connected together, and the belt 4 configured as described above, together with the outer case 31, comes to have an annular shape following along the circumferential direction of the wrist 200. By shaping the belt 4 in an annular shape following along the circumferential direction of the wrist 200, the curler 5 is pressed and elastically deformed to follow along the circumferential direction of the wrist 200 of the wearer of the blood pressure measurement device 1.

As illustrated in FIG. 1 and FIG. 2, the curler 5 is configured in a band-like shape that curves in such a manner as to follow along the circumferential direction of the wrist 200. The curler 5 is formed so that one end 5*a* and the other end 5*b* are separated from each other. The one end 5*a* is one end located on the palm side of the wrist 200 in a state where the blood pressure measurement device 1 is mounted on the wrist 200. The other end 5*b* is one end located on the hand back side of the wrist 200 in a state where the blood pressure measurement device 1 is mounted on the wrist 200. For example, the outer circumferential surface of the other end 5*b* side of the curler 5 is fixed to the device main body 3. The curler 5 is formed of a resin material, for example.

The curler 5 is formed so that the length from the device main body 3 to the other end 5*b* is shorter than the length from the device main body 3 to the one end 5*a*. In the curler 5, the short side from the device main body 3 to the other end 5*b* is disposed on the hand back side of the wrist 200. In the curler 5, the long side from the device main body 3 to the one end 5*a* extends from the hand back side of the wrist 200 to the palm side of the wrist 200 through one side.

The curler 5 with such a configuration is fixed to the outer case 31 with the one end 5*a* and the other end 5*b* orientated to face the first belt 61 of the belt 4.

The curler 5 has a hardness appropriate to provide flexibility and shape retainability. Here, "flexibility" refers to deformation of the shape of the curler 5 in a radial direction at the time of application of external force of the belt 4 to the curler 5. For example, the "flexibility" refers to deformation of the shape of the curler 5 in a side view in which the curler 5 approaches the wrist 200, is along the shape of the wrist 200, or follows the shape of the wrist 200 when the curler 5 is pressed by the belt 4. Furthermore, "shape retainability"

refers to the ability of the curler 5 to maintain a pre-imparted shape when no external force is applied to the curler 5. For example, the "shape retainability" refers to, in the present embodiment, the ability of the curler 5 to maintain the shape in a shape curving along the circumferential direction of the wrist 200.

The cuff structure 6 is disposed on the inner circumferential surface of the curler 5. The curler 5 holds a portion of the cuff structure 6 along the shape of an inner circumferential surface 5*c* of the curler 5. For example, the curler 5 holds the cuff structure 6 by fixing the cuff structure 6 by a joining layer provided between the curler 5 and the cuff structure 6. The joining layer is, for example, an adhesive or a double-sided tape.

As illustrated in FIG. 1 to FIG. 3, the cuff structure 6 includes the pressing cuff 71, a back plate 72, a sensing cuff 73, and a wall portion 76. Also, the cuff structure 6 includes a joining layer 75 for joining components each other and joining the curler 5 and the pressing cuff 71.

In the cuff structure 6, the pressing cuff 71, the back plate 72, and the sensing cuff 73 are stacked one another and disposed on the curler 5. As a specific example, as illustrated in FIG. 1 and FIG. 2, in the cuff structure 6, the pressing cuff 71 is fixed to the inner circumferential surface 5*c* of the curler 5. Further, the back plate 72 is fixed to the inner circumferential surface of the pressing cuff 71 on the palm side of the wrist 200 from the inner circumferential surface of the pressing cuff 71 toward the wrist 200. Further, the sensing cuff 73 is fixed to the inner circumferential surface of the back plate 72 on the palm side. Each member of the cuff structure 6 is fixed to the member adjacent thereto in the stacking direction by the joining layer.

The pressing cuff 71 is fluidly connected to a pump through a flow path portion. The pressing cuff 71 is configured in a band-like shape extending in one direction. A portion of the pressing cuff 71 is fixed to the inner circumferential surface 5*c* of the curler 5 by the joining layer. In addition, the pressing cuff 71 has a length capable of pressing the sensing cuff 73 toward the wrist 200 side and pressing the hand back side of the wrist 200 in a state where the blood pressure measurement device 1 is mounted. The pressing cuff 71 has a length extending from the one end 5*a* to the other end 5*b* of the inner circumferential surface 5*c* of the curler 5, for example.

As illustrated in FIG. 3 and FIG. 4, the pressing cuff 71 includes an air bag 81 and a connection portion 84 provided on the air bag 81. In the above-described example, a configuration in which one air bag 81 is used has been described as an example, but the present invention is not limited thereto. In another example, a plurality of the air bags 81 may be provided, and the plurality of air bags 81 may be stacked. In a configuration in which the plurality of air bags 81 are used, the plurality of stacked air bags 81 fluidly communicate with each other in, for example, the stacking direction.

The pressing cuff 71 with such a configuration is configured by integrally welding a plurality of sheet members 86 together. The connection portion 84 is connected to the flow path portion of the device main body 3. The connection portion 84 is connected to the flow path portion, and thus the pressing cuff 71 is fluidly connected to the pump.

Here, the air bag 81 is a bag-like structure, and in the present embodiment, the blood pressure measurement device 1 is configured to use air with the pump, and thus the present embodiment will be described using the air bag. However, in a case where a fluid other than air is used, the bag-like structure may be a fluid bag that is inflated by the fluid.

The air bag 81 is formed in a rectangular bag-like shape that is long in one direction. Additionally, the air bag 81 is set so that the width in the lateral direction is the same as the width in the lateral direction of the curler 5. The air bag 81 is configured by, for example, combining two sheet members 86 and thermally welding the sheet members 86 in a rectangular frame shape that is long in one direction, as illustrated in a welded portion 81*a* in FIG. 3.

The connection portion 84 is, for example, a nipple. The connection portion 84 is connected to the flow path portion of the device main body 3. The connection portion 84 is provided on a portion facing the device main body 3 of the air bag 81. The leading end of the connection portion 84 is exposed from a sheet member 86 facing the curler 5, of the two sheet members 86 forming the air bag 81. The connection portion 84 is connected to the flow path portion.

As illustrated in FIG. 3, the back plate 72 is formed in a plate shape that is long in one direction. The back plate 72 is attached to the outer surface of the sheet of the pressing cuff 71 on the wrist 200 side by the joining layer. The back plate 72 has a length such that the back plate 72 faces a region where an artery 210 and a tendon 220 are present in a state where the blood pressure measurement device 1 is mounted on the wrist 200.

The back plate 72 has shape followability. Here, "shape followability" refers to a function in which the back plate 72 can be deformed in such a manner as to follow the shape of a contacted portion of the wrist 200 to be disposed. This contacted portion of the wrist 200 refers to a region of the wrist 200 that faces the back plate 72. This contact includes both direct contact and indirect contact via the sensing cuff 73.

Further, as illustrated in FIG. 3, the back plate 72 includes a plurality of grooves 72*a* formed in both main surfaces of the back plate 72 and extending in a direction orthogonal to the longitudinal direction. A plurality of the grooves 72*a* are provided on both main surfaces of the back plate 72. The plurality of grooves 72*a* provided on both main surfaces face each other in the thickness direction of the back plate 72. Additionally, the plurality of grooves 72*a* are disposed at equal intervals in the longitudinal direction of the back plate 72.

In the back plate 72, portions including the plurality of grooves 72*a* are thinner than portions including no grooves 72*a* and thus the portions including the plurality of grooves 72*a* are easily deformed. Accordingly, the back plate 72 is deformed in such a manner as to follow the shape of the wrist 200, and has shape followability of extending in the circumferential direction of the wrist 200. The back plate 72 is formed such that the length of the back plate 72 is sufficient to cover the palm side of the wrist 200. The back plate 72 transfers the pressing force from the pressing cuff 71 to the back plate 72 side main surface of the sensing cuff 73 in a state where the back plate 72 is extending along the shape of the wrist 200.

The sensing cuff 73 is fluidly connected to the pump via the flow path portion of the device main body 3. The sensing cuff 73 is fixed to the main surface of the back plate 72 on the wrist 200 side by the joining layer.

The sensing cuff 73 has such a length that the sensing cuff 73 comes into contact with a region of the wrist 200 where the artery 210 is present in a state where the blood pressure measurement device 1 is mounted on the wrist 200. As an example, the sensing cuff 73 has a length extending from a radial artery 211 to an ulnar artery 212 of the artery 210, as illustrated in FIG. 3.

For example, the sensing cuff 73 is formed in the same shape as that of the back plate 72 or a shape that is smaller than that of the back plate 72, in the longitudinal direction and the width direction of the back plate 72. In the sensing cuff 73, the region of the wrist 200 where the artery 210 on the palm side is present is compressed via the inflated pressing cuff 71 by being supplied with the air and pressed by the inflated pressing cuff 71. The sensing cuff 73 is pressed by the inflated pressing cuff 71 toward the wrist 200 side with the back plate 72 in between.

For example, as illustrated in FIG. 3, the sensing cuff 73 includes one air bag 91, a flow path body 92 that communicates with the air bag 91, and a connection portion 93 provided at the leading end of the flow path body 92. One main surface of the air bag 91 of the sensing cuff 73 is fixed to the back plate 72. The sensing cuff 73 is joined to the main surface of the back plate 72 on the wrist 200 side by the joining layer. The sensing cuff 73 with such a configuration is constituted by welding two sheet members 96.

Here, the air bag 91 is a bag-like structure, and in the present embodiment, the blood pressure measurement device 1 is configured to use air with the pump, and thus the present embodiment will be described using the air bag. However, in a case where a fluid other than air is used, the bag-like structure may be a fluid bag that is inflated by the fluid.

The air bag 91 is constituted in a rectangular shape that is long in one direction. The air bag 91 is configured by, for example, combining the two sheet members 96 that are long in one direction and thermally welding the sheet members 96 in a rectangular frame shape that is long in one direction, as illustrated in a welded portion 91*a* in FIG. 3.

The flow path body 92 is integrally provided at a portion of one edge portion of the air bag 91 in the longitudinal direction. As a specific example, the flow path body 92 is provided at the end portion of the air bag 91 near the device main body 3. Additionally, the flow path body 92 is formed in a shape that is long in one direction and has less width than the width of the air bag 91 in the lateral direction, and formed with a leading end having a circular shape. The flow path body 92 includes the connection portion 93 on the leading end. The flow path body 92 is connected to the flow path portion of the device main body 3 via the connection portion 93, and configures a flow path between the flow path portion and the air bag 91.

The flow path body 92 is configured by thermally welding a portion of sheet members 96, which is adjacent to a region of the sheet members 96 constituting the air bag 91, in a frame shape long in one direction, in a state where the connection portion 93 is disposed on the two sheet members 96. The flow path body 92 and the connection portion 93 are disposed on the curler 5 side with respect to the pressing cuff 71 by disposing a portion of the flow path body 92 in, for example, a cut formed in the pressing cuff 71. Alternatively, the connection portion 93 may be connected to the flow path portion of the device main body 3 through a hole formed in the pressing cuff 71, for example.

Note that, a portion of the welded portion 91*a*, where the two sheet members 96 are welded in a rectangular frame shape, is not welded and the air bag 91 is constituted to be continuous with a welded portion 92*a* constituting the flow path body 92, and thus the air bag 91 and the flow path body 92 fluidly communicate with each other.

The connection portion 93 is, for example, a nipple. The connection portion 93 is provided at the leading end of the flow path body 92. Also, the leading end of the connection portion 93 is externally exposed from the sheet member 96 facing the curler 5 and the back plate 72, of the two sheet members 96 constituting the flow path body 92. The connection portion 93 is connected to the flow path portion.

The wall portion 76 is provided along at least one of the pair of edge portions along the longitudinal direction of the sensing cuff 73. Further, the wall portion 76 has a length such that the wall portion 76 faces the region of the wrist 200 where the tendon 220 is present when the blood pressure measurement device 1 is mounted on the wrist 200. In the present embodiment, as illustrated in FIG. 3, the wall portion 76 has a length extending from the one end to the other end in the longitudinal direction of the air bag 91 of the sensing cuff 73 as an example. Additionally, the wall portion 76 is provided on the back plate 72, for example. The wall portion 76 may be integrally formed in the back plate 72. Alternatively, the wall portion 76 may be formed by fixing a member separate from the back plate 72 to the back plate 72.

The wall portion 76 is disposed at a position adjacent to each of the pair of edge portions along the longitudinal direction of the sensing cuff 73, of the back plate 72. That is, a pair of wall portions 76 is provided. Also, each of the pair of wall portions 76 is provided at an edge portion along the longitudinal direction of the back plate 72, for example. The pair of wall portions 76 is curved along the curler 5 in a state where the cuff structure 6 is fixed to the curler 5.

As illustrated in FIG. 2, the wall portion 76 has a height such that the wall portion 76 can be adhered to the wrist 200 to push the wrist 200 and bring the sensing cuff 73 adhered to the wrist 200 in a state where the blood pressure measurement device 1 is mounted on the wrist 200, air is supplied to the sensing cuff 73, and the pressing cuff 71 is inflated. Here, in the present embodiment, the height of the wall portion 76 is a height from the main surface on the wrist 200 side of the back plate 72 to a leading end surface 76*a* of the wall portion 76.

In other words, as illustrated in FIG. 6, a height H1 from the main surface of the back plate 72 on the wrist 200 side to the leading end surface 76*a* of the wall portion 76 in a state where the blood pressure measurement device 1 is mounted on the wrist 200, air is supplied to the sensing cuff 73, and the pressing cuff 71 is inflated, is greater than a height H2 from the main surface of the back plate 72 on the wrist 200 side to the protruding end of the sensing cuff 73 in the inflated state on the wrist 200 side. In the present embodiment, as an example, the height of the wall portion 76 is constant from the one end to the other end in the longitudinal direction of the wall portion 76.

In the present embodiment, for example, the wall portion 76 has a height such that the wall portion 76 protrudes beyond the sensing cuff 73 when the sensing cuff 73 is inflated in a state where the blood pressure measurement device 1 is not mounted on the wrist 200. Here, the non-mounting state where the blood pressure measurement device 1 is not mounted on the wrist 200 means a state where the blood pressure measurement device 1 is not attached on the wrist 200. That is, the wrist 200 is not disposed in the curler 5.

As illustrated in FIG. 3, each of the pair of wall portions 76 has a plurality of grooves 76*b* formed on the leading end surface 76*a*. The plurality of grooves 76*b* extend in a direction orthogonal to the longitudinal direction of the leading end surface 76*a*. The plurality of grooves 76*b* extend from one edge along the longitudinal direction of the leading end surface 76*a* to the other edge. The plurality of grooves 76*b* are disposed at equal intervals in the longitudinal direction of the wall portions 76.

As illustrated in FIG. 3, the plurality of grooves 76*b* on the leading end surface 76*a* of one wall portion 76 are formed in the same number as the grooves 72*a* of the back plate 72, for example. The plurality of grooves 76*b* are aligned with the grooves 72*a* of the back plate 72 in a direction orthogonal to the longitudinal direction of the leading end surface 76*a*. Additionally, the extending direction of the plurality of grooves 76*b* is parallel to the extending direction of the plurality of grooves 72*a*. In other words, the grooves 76*b* of one leading end surface 76*a*, the grooves 72*a*, and the grooves 76*b* of the other leading end surface 76*a* are linearly aligned in a direction orthogonal to the longitudinal direction of the leading end surface 76*a* in a plan view as illustrated in FIG. 3.

In the pair of wall portions 76, portions including the plurality of grooves 76*b* are lower in height than portions including no grooves 76*b* and thus the portions including the plurality of grooves 76*b* are easily deformed. Accordingly, the pair of wall portions 76 is deformed in such a manner as to follow the shape of the wrist 200, and has shape followability of extending in the circumferential direction of the wrist 200.

In the blood pressure measurement device 1 configured in this manner, the pair of wall portions 76 is pressed against the region of the wrist 200 where the artery 210 is present in a state in which the blood pressure measurement device 1 is mounted on the wrist 200, air is supplied to the sensing cuff 73, and the pressing cuff 71 is inflated.

In other words, by attaching the blood pressure measurement device 1 to the wrist 200 and tightening the belt 4, the pair of wall portions 76 presses the region of the wrist 200 where the artery is present. Furthermore, the pressing cuff 71 is inflated so that the wall portion 76 further presses the region of the wrist 200 where the artery 210 is present.

By the pair of wall portions 76 pressing the region of the wrist 200 where the artery is present, the unevenness of the region of the wrist 200 where the artery is present is reduced. Here, the unevenness of the wrist 200 is unevenness caused by a living body such as the tendon 220, a bone, and a muscle of the wrist 200. Since the unevenness in the region of the wrist 200 where the artery is present is reduced, the sensing cuff 73 is suitably adhered to the wrist.

Furthermore, since the unevenness in the region of the wrist 200 where the artery 210 is present is reduced, it is possible to prevent the sensing cuff 73 from being collapsed even when air is supplied and the sensing cuff 73 is pressed against the wrist 200 by the inflated pressing cuff 71. Here, the collapse means that the wrist 200 side and the back plate 72 side of the inner surface of the sensing cuff 73 come into contact with each other. As a result, it is possible to uniformly inflate the sensing cuff 73. Since the sensing cuff 73 can be inflated uniformly, the pressure inside the sensing cuff 73 can be made uniform. Thus, as illustrated in FIG. 6, the pressure acting on the region of the wrist 200 to which the sensing cuff 73 is adhered can be substantially constant.

Furthermore, since the pair of wall portions 76 presses the region of the wrist 200 where the artery is present, the wrist 200 follows the leading end surface 76*a* of the wall portion 76. Since the wrist 200 follows the leading end surface 76*a* of the wall portion 76, the sensing cuff 73 is suitably adhered to the region of the wrist 200 where the artery 210 is present.

As described above, the pressure in the sensing cuff 73 can be made uniform and the sensing cuff 73 is suitably adhered to the wrist 200, and thus the accuracy of the blood pressure measurement can be improved.

Furthermore, the wall portion 76 has a length such that the wall portion 76 faces the tendon 220 in a state where the blood pressure measurement device 1 is mounted on the wrist 200, and thus the tendon 220 can be pushed into the wrist 200. Therefore, the sensing cuff 73 can be adhered to the region of the wrist 200 where the radial artery 211 to the ulnar artery 212 are present.

Furthermore, the blood pressure measurement device 1 has a configuration in which the blood pressure measurement device 1 includes the pair of wall portions 76, and thus the pair of wall portions 76 presses against the wrist 200. Since the wrist 200 is pressed by the pair of wall portions 76, a portion of the wrist 200 between the pair of wall portions 76 follows the leading end surface 76*a*. Therefore, since the region of the wrist 200 that follows the leading end surface 76*a* of the wall portion 76 can be increased, the sensing cuff 73 can be more suitably adhered to the region of the wrist 200 where the artery 210 is present.

Furthermore, the pair of wall portions 76 is provided on the back plate 72, and thus the pair of wall portions 76 is supported by the back plate 72. Therefore, it is possible to stably press the pair of wall portions 76 toward the wrist 200 side.

Further, the wall portion 76 is pressed toward the wrist 200 by the back plate 72 when the pressing cuff 71 is inflated. Therefore, it is possible to prevent the stress generated on the surface of the pressing cuff 71 from increasing in a state where the blood pressure measurement device 1 is mounted on the wrist 200 and the pressing cuff 71 is inflated by supplying air to the sensing cuff 73.

Furthermore, the pair of wall portions 76 is integrally formed with the back plate 72, and thus the number of parts of the blood pressure measurement device 1 can be prevented from increasing. Thus, the efficiency of the assembling work of the cuff structure 6 can be improved, so the efficiency of the assembling work of the blood pressure measurement device 1 can be improved.

Further, since the plurality of grooves 76*b* are formed on the leading end surface 76*a* of the pair of wall portions 76, the back plate 72 can be easily curved. Therefore, the efficiency of the work of fixing the back plate 72 to the curler 5 can be improved. Further, when the curvature of the curler 5 and the curvature of the wrist 200 are different from each other, the curler 5 is deformed in accordance with the wrist 200 by tightening the belt 4 when the blood pressure measurement device 1 is mounted on the wrist 200. At this time, the wall portion 76 can be easily curved by the plurality of grooves 76*b*, so that the efficiency of mounting work of the blood pressure measurement device 1 can be improved.

Furthermore, the plurality of grooves 76*b* formed on the leading end surface 76*a* of each of the pair of wall portions 76 are aligned with the grooves 72*a* of the back plate 72 in the direction orthogonal to the longitudinal direction of the wall portions 76, so that the bending points of the back plate 72 and the wall portions 76 can coincide with each other.

That is, the back plate 72 is curved as a whole by being bent at the grooves 72*a*, and the wall portion 76 is curved as a whole by being bent at the grooves 76*b*. Since the grooves 72*a* and the grooves 76*b* are aligned with each other, the bending points of the back plate 72 and the wall portion 76 can coincide with each other. Therefore, it is possible to improve the shape followability of the cuff structure 6 to be deformed along the wrist 200.

Further, the wall portion 76 has a height such that the wall portion 76 protrudes beyond the sensing cuff 73 in a state where the blood pressure measurement device 1 is not mounted on the wrist 200 and the sensing cuff 73 is inflated. Therefore, the wall portion 76 presses the wrist 200 in a state where the blood pressure measurement device 1 is mounted on the wrist 200 and the pressing cuff 71 is not inflated.

Then, air is supplied to the sensing cuff 73 in a state where the degree of unevenness of the region of the wrist 200 where the artery is present is reduced by the wall portion 76, and the pressing cuff 71 is inflated. As a result, air can be supplied smoothly to the sensing cuff 73.

As described above, according to the blood pressure measurement device 1 according to the present embodiment, the measurement accuracy of the blood pressure can be improved.

In the above-described example, the wall portion 76 has a height such that the wall portion 76 protrudes beyond the sensing cuff 73 and the sensing cuff 73 can be adhered to the region of the wrist 200 where the artery 210 is present in a state where the blood pressure measurement device 1 is mounted on the wrist 200 and air is supplied to the sensing cuff 73 to inflate the pressing cuff 71. Then, as an example, a configuration is described in which the wall portion 76 has a height such that the wall portion 76 protrudes beyond the sensing cuff 73 in a state where the blood pressure measurement device 1 is not mounted on the wrist 200 and the sensing cuff 73 is inflated. However, the present invention is not limited thereto.

The wall portion 76 may be configured to be lower than the sensing cuff 73 in a state where the blood pressure measurement device 1 is not mounted on the wrist 200 and the sensing cuff 73 is inflated as in a modified example illustrated in FIG. 7, as long as the wall portion 76 can protrude beyond the sensing cuff 73 and the sensing cuff 73 can be adhered to the region of the wrist 200 where the artery is present in a state where the blood pressure measurement device 1 is mounted on the wrist 200, air is supplied to the sensing cuff 73, and the pressing cuff 71 is inflated (H1<H2). Note that in FIG. 7, the pressing cuff 71 and the curler 5 are omitted.

In the blood pressure measurement device 1 of the modified example illustrated in FIG. 7, when the sensing cuff 73 is supplied with air and is pressed against the wrist 200 by the inflated pressing cuff 71, the thickness of the sensing cuff 73 becomes smaller than the thickness of the sensing cuff 73 illustrated in FIG. 7, and the wall portion 76 protrudes beyond the sensing cuff 73.

Alternatively, as in a modified example illustrated in FIG. 8, the wall portion 76 may be configured to have the same height as the sensing cuff 73 in a state where the blood pressure measurement device 1 is not mounted on the wrist 200 and the sensing cuff 73 is inflated (H1=H2).

In the blood pressure measurement device 1 of the modified example illustrated in FIG. 8, when the sensing cuff 73 is supplied with air and is pressed against the wrist 200 by the inflated pressing cuff 71, the thickness of the sensing cuff 73 becomes smaller than the thickness illustrated in FIG. 8, and the wall portion 76 protrudes beyond the sensing cuff 73.

As illustrated in FIG. 7 or FIG. 8, the wall portion 76 may be configured to have a height such that the wall portion 76 protrudes beyond the sensing cuff 73 or have the same height as the sensing cuff 73 in a state where the blood pressure measurement device 1 is not mounted on the wrist 200 and the sensing cuff 73 is inflated. However, since the wall portion 76 is configured to have a height such that the wall portion 76 protrudes beyond the sensing cuff 73 in a state where the blood pressure measurement device 1 is not mounted on the wrist 200 and the sensing cuff 73 is inflated, air is supplied to the sensing cuff 73 in a state where the unevenness of the wrist 200 is reduced by the wall portion 76 by tightening the belt 4. Thus, since air can be supplied smoothly to the sensing cuff 73, the sensing cuff 73 can be more suitably adhered to the region of the wrist 200 where the artery 210 is present. Thus, the wall portion 76 is preferably configured to have a height such that the wall portion 76 protrudes beyond the sensing cuff 73 in a state where the blood pressure measurement device 1 is not mounted on the wrist 200 and the sensing cuff 73 is inflated.

Further, in the above example, the configuration in which the wall portion 76 is integrally formed with the back plate 72 has been described as an example, but the present invention is not limited to this. In another example, the wall portion 76 may be configured to be separately formed with the back plate 72.

For example, when the cuff structure 6 does not include the back plate 72, the wall portion 76 may be integrally formed with the pressing cuff 71. As an example of a configuration in which the cuff structure 6 does not include the back plate 72, there is a configuration in which at least a region of the sheet constituting the surface of the pressing cuff 71 on the wrist 200 side to which the sensing cuff 73 is fixed is formed so as to be able to support the sensing cuff 73 in the same manner as the back plate 72.

Alternatively, in a configuration in which the cuff structure 6 includes the back plate 72, the wall portion 76 may be integrally formed with the pressing cuff 71.

In a case where the wall portion 76 is formed on the pressing cuff 71 as described above, the wall portion 76 is configured on the welded portion 81*a* of the pressing cuff 71 as in a modified example illustrated in FIG. 9, for example. Note that the welded portion 81*a* does not move toward the wrist 200 even when the pressing cuff 71 is inflated. Thus, when the wall portion 76 is formed on the welded portion 81*a*, the wall portion 76 does not move toward the wrist 200 even when the pressing cuff 71 is inflated. In this manner, in the case of the configuration in which the wall portion 76 is formed on a portion that does not move toward the wrist 200 even when the pressing cuff 71 is inflated like the welded portion 81*a* of the pressing cuff 71, the wall portion 76 has a height such that a region of the wrist 200 is pressed where the artery 210 is present in a state where the blood pressure measurement device 1 is mounted.

Alternatively, as an example of a configuration in which the wall portion 76 is formed separately from the back plate 72, the wall portion 76 may be integrally formed on the sensing cuff 73 as in the modified example illustrated in FIG. 10. As an example of the configuration in which the wall portion 76 is provided on the sensing cuff 73, the wall portion 76 may be provided on the welded portion 91*a*. Note that in FIG. 10, the pressing cuff 71 and the back plate 72 are not illustrated.

Further, in the above-described example, the configuration in which the wall portion 76 is formed along each of the pair of edge portions along the longitudinal direction of the sensing cuff 73 has been described as an example, but the configuration is not limited thereto. In another example, as in a modified example illustrated in FIG. 11, the wall portion 76 may be formed along one of the pair of edge portions along the longitudinal direction of the sensing cuff 73. In the case of this configuration, the position at which the wall portion 76 is formed is selected so that the wall portion 76 is located on one of the finger side of the hand with respect to the sensing cuff 73 and the shoulder side with respect to the sensing cuff 73, where the blood pressure can be more suitably measured, in a state where the blood pressure measurement device 1 is mounted on the wrist 200.

In the above-described example, a configuration in which the wall portion 76 has a constant height from the one end to the other end in the direction extending along the sensing cuff 73 has been described as an example, but the present invention is not limited thereto. In another example, the height of the wall portion 76 may not be constant from the one end to the other end in the direction in which the wall portion 76 extends along the sensing cuff 73.

In this manner, as an example of the configuration in which the wall portion 76 has different heights from the one end to the other end in the direction in which the wall portion 76 extends along the edge of the sensing cuff 73 in the longitudinal direction, as illustrated in FIG. 12, the wall portion 76 may be formed in a shape in which the height of a portion of the wrist 200 facing a hard portion such as the tendon 220, a bone, or a muscle is higher than the height of other portions. Note that FIG. 12 illustrates a configuration in which the wall portion 76 is provided on the back plate 72 as an example, and illustrates the side surface of the wall portion 76 and the back plate 72. Note that in the modified example illustrated in FIG. 12, the configuration in which the leading end surface 76*a* of the wall portion 76 is formed into the curved surface is illustrated as an example.

As in the modified example illustrated in FIG. 12, a portion of the wall portion 76 facing a hard living body such as the tendon 220, a bone, or a muscle is configured to have a shape in which such a portion is higher than the other portions, so that the hard portion of the wrist 200 can be pushed in. As a result, the unevenness of the wrist 200 can be reduced.

In the above-described example, the wall portion 76 has a length extending from the one end to the other end in the longitudinal direction of the air bag 91 of the sensing cuff 73. In other words, it has a length extending from the one end to the other end of the edge along the longitudinal direction of the sensing cuff 73. Furthermore, in the present embodiment, as an example, the wall portion 76 has a length extending from the one end to the other end in the longitudinal direction of the back plate 72.

However, the present invention is not limited thereto. In another example, the wall portion 76 may be provided along a portion between the one end and the other end of at least one of the edge portions along the longitudinal direction of the sensing cuff 73. As an example of this, as illustrated in FIG. 13, the wall portion 76 may be formed only in a portion facing a hard living body such as the tendon 220, a bone, or a muscle in a state where the blood pressure measurement device 1 is mounted on the wrist 200. FIG. 13 illustrates a configuration in which the wall portion 76 extends along a portion between the one end and the other end of the sensing cuff 73 in the longitudinal direction. In addition, FIG. 13 illustrates a configuration in which the wall portion 76 is integrally formed with the back plate 72 as an example, and illustrates the side surface of the wall portion 76, the back plate 72, and the air bag 91 of the sensing cuff 73.

In the above-described example, a configuration in which one wall portion 76 is provided along one edge portion along the longitudinal direction of the sensing cuff 73 has been described as an example, but the present invention is not limited thereto. In another example, as in a modified example illustrated in FIG. 14, a plurality of the wall portions 76 may be formed along one edge portion along the longitudinal direction of the sensing cuff 73. In other words, the wall portion 76 may be divided into a plurality of portions. In this manner, the wall portion 76 is configured to be divided into the plurality of portions, and thus the blood pressure measurement device 1 is easily mounted on the wrist 200. Note that FIG. 14 illustrates a configuration in which the wall portion 76 is formed on the back plate 72 as an example, and illustrates the side surface of the wall portion 76 and the back plate 72.

In the above-described example, a configuration of the cuff structure 6 in which a portion of the pressing cuff 71 is disposed on the hand back side of the wrist 200 in a state where the blood pressure measurement device 1 is mounted on the wrist 200 has been described as an example. However, the present invention is not limited to this configuration. In another example, the cuff structure 6 may be configured to include a tensile cuff 74 separate from the pressing cuff 71 as a cuff disposed on the hand back side of the wrist 200 in a state where the blood pressure measurement device 1 is mounted on the wrist 200.

This modified example will be described with reference to FIG. 15 and FIG. 16. FIG. 15 is an explanatory view illustrating a state where the blood pressure measurement device 1 according to the modified example is mounted on the wrist 200.

FIG. 16 is a plan view illustrating a cuff structure 6A of the blood pressure measurement device 1 according to the modified example. FIG. 16 illustrates a surface of the cuff structure 6A on the side of the wrist 200 in a state where the blood pressure measurement device 1 is mounted on the wrist 200.

As illustrated in FIG. 15 and FIG. 16, the cuff structure 6A includes a pressing cuff 71A, the back plate 72, the sensing cuff 73, and the tensile cuff 74. The cuff structure 6A includes a joining layer for joining components each other and joining the curler 5 and the pressing cuff 71.

The pressing cuff 71A is fluidly connected to a pump through a flow path portion. The pressing cuff 71A is inflated to press the back plate 72 and the sensing cuff 73 toward the wrist 200 side. The pressing cuff 71A is configured in a band-like shape extending in one direction. The pressing cuff 71A is fixed to the inner circumferential surface of the curler 5 by the joining layer.

To be specific, the pressing cuff 71A incudes the air bag 81, a flow path body 83 in communication with the air bag 81, and the connection portion 84 provided at a leading end of the flow path body 83.

As illustrated in FIG. 16, the flow path body 83 is provided integrally with a portion of the edge portion at the one end in the longitudinal direction of the air bag 81, for example. As a specific example, the flow path body 83 is provided at the end portion of the air bag 81 near the device main body 3. Additionally, the flow path body 83 is formed in a shape that is long in one direction and has less width than the width of the air bag 81 in the lateral direction and formed with a leading end having a circular shape. The flow path body 83 includes the connection portion 84 on the leading end.

The flow path body 83 is configured by thermally welding a portion of sheet members 86, which is adjacent to a region of the sheet members 86 constituting the air bag 81, in a frame shape long in one direction, in a state where the connection portion 84 is disposed on the two sheet members 86.

Note that, a portion of the welded portion 81*a*, where the two sheet members 86 are welded in a rectangular frame shape, is not welded and the air bag 81 provided with the flow path body 83 are constituted to be continuous with a welded portion 83*a* constituting the flow path body 83, and thus the air bag 81 fluidly communicates with the flow path body 83. The connection portion 84 is connected to the flow path portion.

The tensile cuff 74 is fluidly connected to the pump through the flow path portion. The tensile cuff 74 is fixed to the hand back side of the wrist 200 of the curler 5. The tensile cuff 74 is inflated to press the curler 5 such that the curler 5 is spaced apart from the wrist 200, thereby pulling the belt 4 and the curler 5 toward the hand back side of the wrist 200. The tensile cuff 74 includes, for example, a plurality of air bags 101 and a connection portion 103 provided on the air bag 101 facing the curler 5. The plurality of air bags 101 are, for example, a six layered air bag 101.

Here, the air bag 101 is a bag-like structure, and in the present embodiment, a blood pressure measurement device 1A is configured to use air with the pump, and thus the present embodiment will be described using the air bag. However, in a case where a fluid other than air is used, the bag-like structure may be a fluid bag that is inflated by the fluid. The plurality of air bags 101 are stacked and are in fluid communication with each other in the stacking direction.

The tensile cuff 74 with such a configuration is constituted by welding a plurality of the sheet members 106. The tensile cuff 74 is fixed to the hand back side of the wrist 200 of the curler 5. In other words, the flow path body 83 of the pressing cuff 71A and the flow path body 92 of the sensing cuff 73 are disposed between the curler 5 on the hand back side of the wrist 200 and the tensile cuff 74.

Additionally, the tensile cuff 74 is configured such that the thickness of the tensile cuff 74 in an inflating direction, in the present embodiment, in the direction in which the curler 5 and the wrist 200 face each other, during inflation, is larger than the thickness of the pressing cuff 71A in the inflating direction during inflation and than the thickness of the sensing cuff 73 in the inflating direction during inflation. Specifically, the air bag 101 of the tensile cuff 74 includes more layer structures than an air bag 81A in the pressing cuff 71A and the air bag 91 in the sensing cuff 73, and is greater in thickness than the pressing cuff 71A and the sensing cuff 73 when the air bag 101 is inflated from the curler 5 toward the wrist 200.

The air bag 101 is formed in a rectangular bag-like shape that is long in one direction. Additionally, the air bag 101 is set so that the width in the lateral direction is the same as the width in the lateral direction of the curler 5. The air bag 101 is formed by, for example, combining two sheet members 106 and thermally welding the sheet members 106 in a rectangular frame shape that is long in one direction, as illustrated in a welded portion 101*a* in FIG. 16. The six layered air bag 101 are in fluid communication with each other through openings provided on the sheet members 106 facing one another.

The connection portion 103 is, for example, a nipple. The connection portion 103 is provided on the air bag 101 disposed adjacent to the curler 5. The leading end of the connection portion 103 is exposed from the sheet member 106 facing the curler 5, of the two sheet members 106 constituting the air bag 101. The connection portion 103 is connected to the flow path portion of the device main body 3.

That is, the present invention is not limited to the embodiments described above, and various modifications can be made in an implementation stage within a range that does not depart from the gist of the present invention. Furthermore, each of the embodiments may be implemented in combination as appropriate to the extent possible, and in this case, combined effects can be obtained. Also, the embodiments described above include various stages of invention, and various inventions may be extracted by appropriately combining the described plurality of disclosed constituent elements. For example, in a case where the problem can be solved and the effects can be obtained even when some constituent elements are removed from the entire constituent elements given in the embodiment, the configuration obtained by removing the constituent elements may be extracted as an invention.

REFERENCE NUMERALS LIST

1 Blood pressure measurement device
3 Device main body
4 Belt
5 Curler
6 Cuff structure
11 Case
12 Display unit
13 Operation unit
31 Outer case
31*a* Lug
31*b* Spring rod
32 Windshield
41 Button
61 First belt
61*a* Belt portion
61*b* Buckle
61*e* Frame body
61*f* Prong
62 Second belt
62*a* Small hole
71 Pressing cuff
72 Back plate
72*a* Groove
73 Sensing cuff
74 Tensile cuff
81 Air bag
84 Connection portion
86 Sheet member
91 Air bag
92 Flow path body
93 Connection portion
96 Sheet member
101 Air bag
103 Connection portion
106 Sheet member
200 Wrist
210 Artery
211 Radial artery
212 Ulnar artery
220 Tendon

What is claimed is:

1. A cuff structure comprising:

a sensing cuff configured in a shape that is long in one direction, the sensing cuff configured to come into contact with a region of a wrist where an artery is present;

a pressing cuff configured in a shape that is long in one direction, the pressing cuff provided on a side of the sensing cuff opposite from a wrist side surface, the pressing cuff configured to press the sensing cuff against the wrist by being inflated; and a wall portion provided on the sensing cuff or the pressing cuff along at least one edge portion along a longitudinal direction of the sensing cuff, the wall portion having a leading end surface configured to come into contact with the wrist, wherein the wall portion has a height H1 such that the wall portion protrudes beyond a height H2 of the sensing cuff and the sensing cuff is adhered to the wrist in a state where the sensing cuff is inflated, and wherein the height H1 of the wall portion is configured to enable uniform presence of fluid in the sensing cuff, wherein the wall portion further includes a plurality of grooves orthogonal to the longitudinal direction and formed on the leading end surface, which are configured so that said wall portion can curve to conform to curvature of said contacted region of said wrist.

2. A blood pressure measurement device comprising:

a device main body;

a curler provided on the device main body; and a cuff structure provided on the curler, the cuff structure including:

a sensing cuff configured in a shape that is long in one direction, the sensing cuff configured to come into contact with a region of a wrist where an artery is present;

a pressing cuff configured in a shape that is long in one direction, the pressing cuff provided on a side of the sensing cuff opposite from a wrist side surface, the pressing cuff configured to press the sensing cuff against the wrist by being inflated; and a wall portion provided on the sensing cuff or the pressing cuff along at least one edge portion along a longitudinal direction of the sensing cuff, the wall portion having a leading end surface configured to come into contact with the wrist, wherein the wall portion has a height H1 such that the wall portion protrudes beyond a height H2 of the sensing cuff and the sensing cuff is adhered to the wrist in a state where the sensing cuff is inflated, and wherein the height H1 of the wall portion is configured to enable uniform presence of fluid in the sensing cuff, wherein the wall portion further includes a plurality of grooves orthogonal to the longitudinal direction and formed on the leading end surface, which are configured so that said wall portion can curve to conform to curvature of said contacted region of said wrist.

* * * * *